United States Patent
Ho et al.

(10) Patent No.: US 10,271,821 B2
(45) Date of Patent: Apr. 30, 2019

(54) METHOD OF ULTRASOUND IMAGING AND ULTRASOUND SCANNER

(71) Applicant: Industrial Technology Research Institute, Hsinchu (TW)

(72) Inventors: Chung-Lien Ho, Hsinchu (TW); Yi-Ting Wang, Hsinchu County (TW); Ren-Jr Chen, Hsinchu (TW); Chu-Yu Huang, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 1060 days.

(21) Appl. No.: 14/580,221

(22) Filed: Dec. 23, 2014

(65) Prior Publication Data

US 2016/0174941 A1 Jun. 23, 2016

(51) Int. Cl.
| | | |
|---|---|---|
| *A61B 8/00* | (2006.01) | |
| *A61B 8/08* | (2006.01) | |
| *G01S 7/52* | (2006.01) | |
| *G01S 15/89* | (2006.01) | |
| *G10K 11/34* | (2006.01) | |
| *A61B 8/14* | (2006.01) | |

(52) U.S. Cl.
CPC .......... *A61B 8/5207* (2013.01); *A61B 8/4483* (2013.01); *G01S 7/52028* (2013.01); *G01S 15/8915* (2013.01); *G10K 11/346* (2013.01); *A61B 8/14* (2013.01); *A61B 8/461* (2013.01); *A61B 8/469* (2013.01)

(58) Field of Classification Search
None
See application file for complete search history.

(56) References Cited

U.S. PATENT DOCUMENTS

| | | | |
|---|---|---|---|
| 4,972,358 A | * | 11/1990 | Welles, II ............. G06F 17/142 708/405 |
| 5,720,708 A | | 2/1998 | Lu et al. |
| 6,551,246 B1 | | 4/2003 | Ustuner et al. |
| 6,685,641 B2 | | 2/2004 | Liu |

(Continued)

FOREIGN PATENT DOCUMENTS

| | | |
|---|---|---|
| CN | 103852748 | 6/2014 |
| TW | 202496 | 3/1993 |

(Continued)

OTHER PUBLICATIONS

Romana, "Zoom FFT Algorithm in Ultrasonic Blood Flow Analysis Using MATLAB", International Journal of Scientific and Research Publications, vol. 4, Issue 10, Oct. 2014.*

(Continued)

*Primary Examiner* — Jonathan Cwern
(74) *Attorney, Agent, or Firm* — JCIPRNET (57) ABSTRACT

A method of ultrasound imaging and a corresponding ultrasound scanner are provided. The method includes the steps of receiving an echo signal induced by an ultrasonic plane wave transmission from a transducer of an ultrasound scanner, resampling the echo signal in time domain and/or space domain, performing a spectrum zooming on a band of interest (BOI) of an input signal, performing a Fourier transform on a result of the spectrum zooming, and generating an ultrasound image based on a result of the Fourier transform. The input signal is generated based on the resampling of the echo signal.

22 Claims, 10 Drawing Sheets

(56) References Cited

U.S. PATENT DOCUMENTS

| | | | |
|---|---|---|---|
| 7,957,609 | B2 | 6/2011 | Lu et al. |
| 8,491,475 | B2 | 7/2013 | Ogasawara |
| 8,496,585 | B2 | 7/2013 | Lu |
| 2006/0058662 | A1 | 3/2006 | Kobayashi et al. |
| 2006/0173313 | A1 | 8/2006 | Liu et al. |
| 2009/0036772 | A1 | 2/2009 | Lu |
| 2009/0066727 | A1 | 3/2009 | Lu et al. |
| 2009/0088641 | A1 | 4/2009 | Baba et al. |
| 2011/0144497 | A1* | 6/2011 | Kim .................. A61B 8/00 600/443 |
| 2013/0172752 | A1 | 7/2013 | Hu et al. |
| 2013/0258805 | A1 | 10/2013 | Hansen et al. |
| 2013/0271757 | A1 | 10/2013 | Kang et al. |
| 2013/0340125 | A1 | 12/2013 | Jesse et al. |

FOREIGN PATENT DOCUMENTS

| | | |
|---|---|---|
| TW | 565694 | 12/2003 |
| TW | 201325555 | 7/2013 |

OTHER PUBLICATIONS

Rabiner et al., "The chirp z-transform algorithm," IEEE Transactions on Audio and Electroacoustics, Jun. 1969, pp. 86-92.

Hoyer et al., "The zoom FFT using complex modulation," IEEE International Conference on Acoustics, Speech, and Signal Processing, May 1977, pp. 78-81.

Vaidyanathan et al., "Multirate digital filters, filter banks, polyphase networks, and applications: a tutorial," Proceedings of the IEEE, Jan. 1990, pp. 56-93.

Nayebi et al., " Nonuniform filter banks: a reconstruction and design theory, " IEEE Transactions on Signal Processing, Mar. 1993, pp. 1114-1127.

Jian-Yu Lu, "2D and 3D high frame rate imaging with limited diffraction beams," IEEE Transactions on Ultrasonics, Ferroelectrics, and Frequency Control, Jul. 1997, pp. 839-856.

Jian-Yu Lu, "Experimental study of high frame rate imaging with limited diffraction beams," IEEE Transactions on Ultrasonics, Ferroelectrics, and Frequency Control, Jan. 1998, pp. 84-97.

Vo et al., "Non-uniform DFT filter banks design with semi-definite programming," Proceedings of the 3rd IEEE International Symposium on Signal Processing and Information Technology, 2003, pp. 42-45.

Cheng et al., "Extended high-frame rate imaging method with limited-diffraction beams," IEEE Transactions on Ultrasonics, Ferroelectrics, and Frequency Control, May 2006, pp. 880-899.

Holfort et al., "Plane wave medical ultrasound imaging using adaptive beamforming," 5th IEEE Sensor Array and Multichannel Signal Processing Workshop, Jul. 21-23, 2008, pp. 288-292.

Montaldo et al., "Coherent plane-wave compounding for very high frame rate ultrasonography and transient elastography," IEEE Transactions on Ultrasonics, Ferroelectrics, and Frequency Control, Mar. 2009, pp. 489-506.

Peng et al., "High frame rate ultrasonic imaging through Fourier transform using an arbitrary known transmission field," Fourier Transforms—Approach to Scientific Principles, Apr. 2011, pp. 262-280.

Jeremy Bercoff, "Ultrafast Ultrasound Imaging," Ultrasound Imaging—Medical Application, Aug. 2011, pp. 3-24.

Hu et al., "Improved plane-wave high frame rate imaging using retrospective transmit focusing and filter-derived coherence-index weighting," IEEE Ultrasonics Symposium (IUS), Oct. 11-14, 2010, pp. 1916-1919.

Kruizinga et al., "Plane-wave ultrasound beamforming using a nonuniform fast fourier transform," IEEE Transactions on Ultrasonics, Ferroelectrics, and Frequency Control, Dec. 2012, pp. 2684-2691.

Chu-Yu Huang et al., "Ultrasound apparatus and ultrasound method for beamforming with a plane wave transmission," Unpublished U.S. Appl. No. 14/251,299, filed Apr. 11, 2014.

"Office Action of Taiwan Counterpart Application", dated Sep. 12, 2016, p. 1-p. 4, in which the listed references were cited.

* cited by examiner

METHOD OF ULTRASOUND IMAGING AND ULTRASOUND SCANNER

TECHNICAL FIELD

The disclosure relates to a method of ultrasound imaging and an ultrasound scanner.

BACKGROUND

Ultrasound imaging is widely used in medical diagnosis for visualizing internal body structures including tendons, muscles, joints, vessels and internal organs for possible pathology or lesions. Ultrasound imaging is also widely used for examining pregnant women and their babies.

The conventional two-dimensional (2-D) B-mode ultrasound image uses a line scan mechanism with a focusing wave at the transmitter and a time-domain delay-and-sum (DAS) beamforming at the receiver. To an object at a depth of 5-10 cm, due to the line scan mechanism and possible transmit/receive dynamic focusing, the frame rate, in general, can reach to up to 30-60 frames per second.

However, a 'one-shot' imaging mechanism with a plane wave transmission and a frequency-domain beamforming at the receiver for computational reason is used in high frame rate (HFR) ultrasound image. In this case, due to the one-shot image mechanism, the frame rate is capable of reaching 3000-6000 frames per second.

SUMMARY

The disclosure is directed to a method of ultrasound imaging and an ultrasound scanner, which provide a new method for HFR ultrasound image with plane wave transmission using the spectrum zooming technique based on the spectral property of the ultrasound image.

An embodiment of the disclosure provides a method of ultrasound imaging. The method includes the steps of receiving an echo signal induced by an ultrasonic plane wave transmission from a transducer of an ultrasound scanner, resampling the echo signal in time domain and/or space domain, performing a spectrum zooming on a band of interest (BOI) of an input signal, performing a Fourier transform on a result of the spectrum zooming, and generating an ultrasound image based on a result of the Fourier transform. The input signal is generated based on the resampling of the echo signal.

Another embodiment of the disclosure provides an ultrasound scanner, which includes a transducer and a processor coupled to the transducer. The processor receives an echo signal induced by an ultrasonic plane wave transmission from the transducer, resamples the echo signal in time domain and/or space domain, performs a spectrum zooming on a BOI of an input signal, performs a Fourier transform on a result of the spectrum zooming, and generates an ultrasound image based on a result of the Fourier transform. The input signal is generated based on the resampling of the echo signal.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF DISCLOSED EMBODIMENTS

Figure 1:
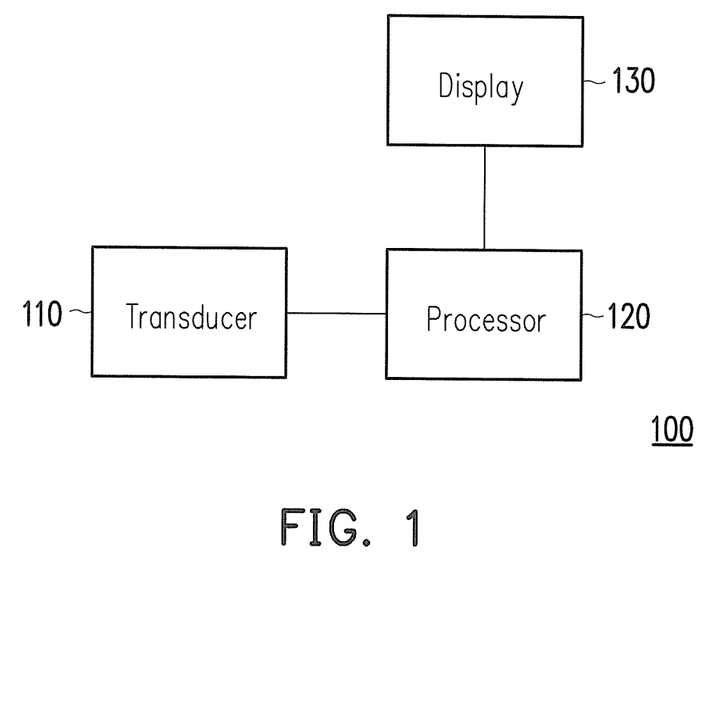
FIG. 1 is a schematic diagram showing an ultrasound scanner according to an embodiment.

FIG. 1 is a schematic diagram showing an ultrasound scanner 100 according to an embodiment. The ultrasound scanner 100 includes a transducer 110, a processor 120, and a display 130. The processor 120 is coupled to the transducer 110 and the display 130. The processor 120 may control the transducer 110 to transmit an ultrasonic plane wave and control the transducer 110 to receive the echo signal induced by the ultrasonic plane wave transmission. The processor 120 may execute the method of ultrasound imaging shown in FIG. 2A or FIG. 2B to generate an ultrasound image, and then the processor 120 may store the ultrasound image or control the display 130 to display the ultrasound image.

Figure 2A:
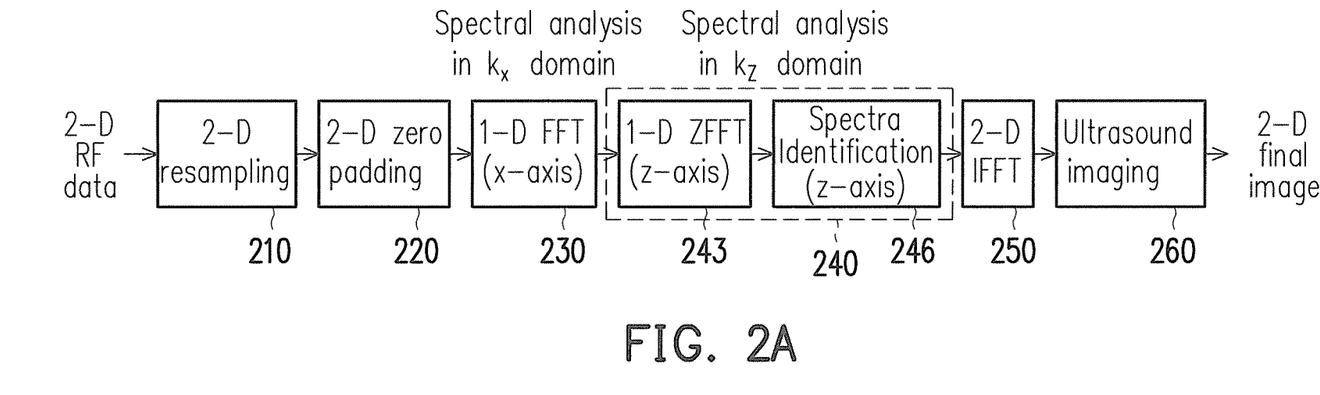
FIG. 2A is a flow chart showing a method of ultrasound imaging according to an embodiment.

FIG. 2A is a flow chart showing a method of ultrasound imaging according to an embodiment. This method of ultrasound imaging may be executed by the processor 120. Initially, the processor 120 receives the echo signal induced by the ultrasonic plane wave transmission from the transducer 110. The echo signal is arranged in a two-dimensional (2-D) format. The two dimensions are corresponding to an axial direction ($k_z$ space domain) and a lateral direction ($k_x$ space domain) with respect to the transducer 110. The axial direction and the lateral direction are orthogonal.

In step 210, the processor 120 performs 2-D resampling on the echo signal in time domain and/or space domain. When the number of samples of the result of step 210 is not a power of two, the processor 120 performs 2-D zero padding on the result of step 210 in step 220 to make the number of samples a power of two.

In step 230, the processor 120 performs spectral analysis on the result of step 220 in $k_x$ domain. This spectral analysis is implemented by a one-dimensional (1-D) fast Fourier transform (FFT) on the x-axis.

In step 240, the processor 120 performs spectral analysis on the result of step 230 in $k_z$ domain. This spectral analysis is implemented by a 1-D ZFFT on the z-axis in step 243 followed by spectra identification on the z-axis in step 246. ZFFT means spectrum zooming followed by a 1-D FFT on the z-axis. The spectrum zooming is explained in details below. The processor 120 performs the spectra identification in step 246 to estimate a plurality of target spectral lines that are non-uniformly distributed in $k_z$ domain.

In step 250, the processor 120 performs a 2-D inverse fast Fourier transform (IFFT) based on the target spectral lines. In step 260, the processor 120 generates the final ultrasound image by converting the signal amplitudes of the result of the IFFT into gray level values of pixels of the ultrasound image. In an embodiment, the gray level value of each pixel of the ultrasound image may be directly proportional to the corresponding signal amplitude. In another embodiment, the gray level value of each pixel of the ultrasound image may be inversely proportional to the corresponding signal amplitude.

Figure 2B:
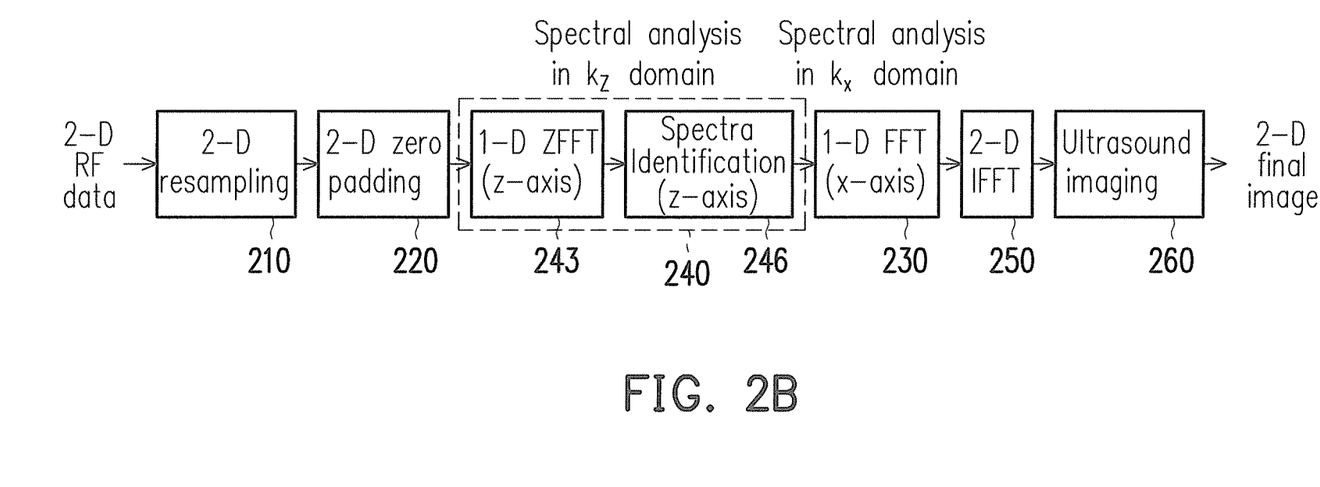
FIG. 2B is a flow chart showing a method of ultrasound imaging according to another embodiment.

FIG. 2B is a flow chart showing a method of ultrasound imaging according to another embodiment. This method of ultrasound imaging may be executed by the processor 120. In FIG. 2B, the execution orders of steps 230 and 240 are exchanged. In other words, step 240 is executed before step 230.

Figure 3:
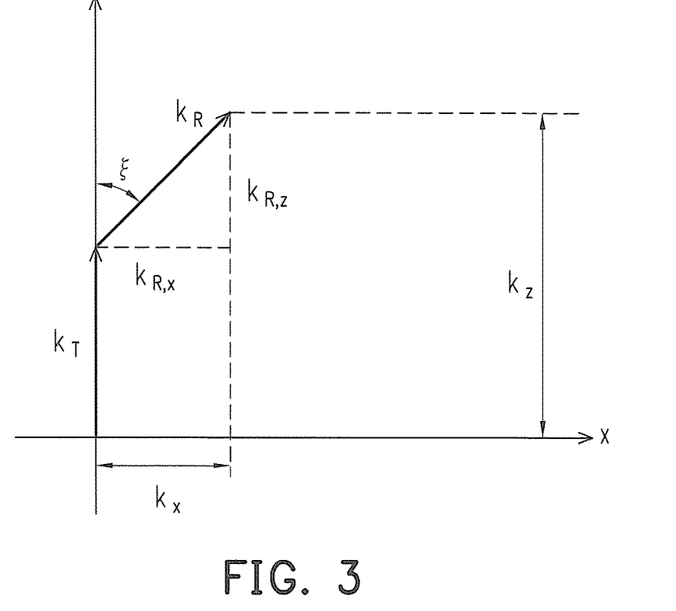
FIG. 3 and FIG. 4 are schematic diagrams showing spatial frequencies of 2-D ultrasound images according to an embodiment.

FIG. 3 is a schematic diagram showing spatial frequencies of a 2-D ultrasound image with plane wave transmission according to an embodiment. The transmit spatial frequency $k_T$ and receive spatial frequency $k_R$ of a 2-D ultrasound image are depicted in FIG. 3. The spatial frequencies are also known as wave numbers. Without loss generality, it is assumed that a plane wave with a spatial frequency k is transmitted in direction z (i.e. axial direction), which is normal to the 1-D linear array of the transducer 110, and the echo is received at the linear array at an angle of ξ with respect to the axial direction. The echo induces two components in directions z and x (i.e. lateral direction) as $k_{R,z}$ and $k_{R,x}$. By referring to FIG. 3, clearly the transmit and receive spatial frequencies $k_T$ and $k_R$ can therefore be respectively represented as $k_T=k$ and $k_R=k=k_{R,x}+k_{R,z}=k\sin \xi + k\cos \xi$. $k_x=k_{R,x}=k\sin\xi$. $k_z=k_T+k_{R,z}=k+k\cos \xi$. $k^2=k_{R,x}^2+k_{R,z}^2=k_x^2+(k_z-k)^2$. With some manipulations, we have the following equation (1).

$$k = \frac{k_x^2 + k_z^2}{2k_z} \quad (1)$$

Equation (1) definitely shows that for a 2-D ultrasound image k is a nonlinear (quadratic) function of $k_x$ and $k_z$. So we can further conclude that the spatial frequency k is non-uniformly sampled in $k_z$ direction (domain). This non-uniform sampling is considered in the spectra identification in step 246.

Figure 4:
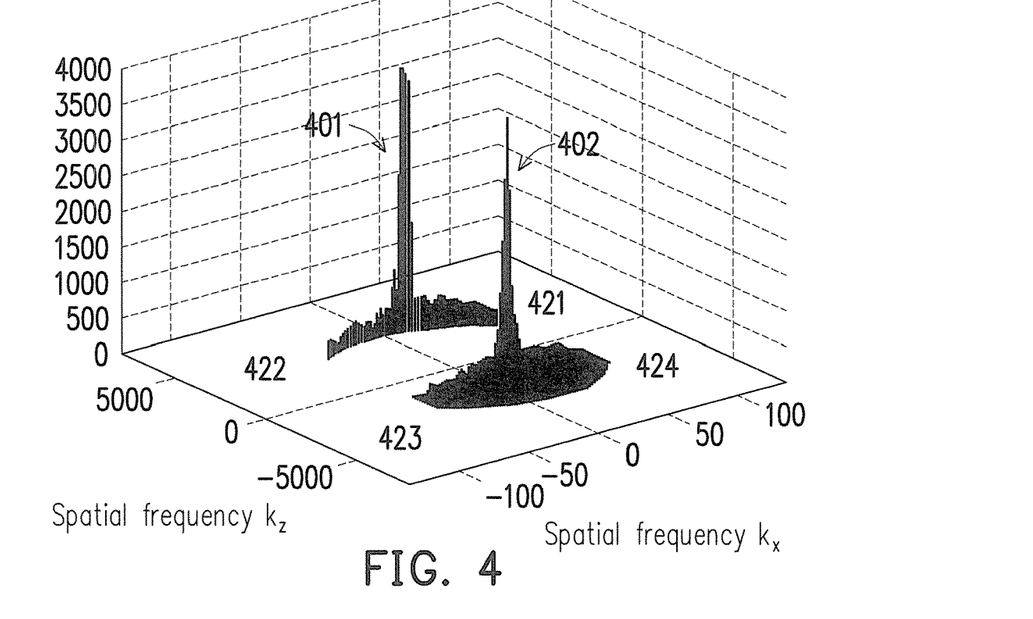

The spectrum zooming technique in the ZFFT in step 243 is based on the spectral property of ultrasound image. Specifically, the spectral property depends on the parameters of the transducer 110 regardless of the type of measurement objects. The spectral property includes localized property and symmetric property as shown in FIG. 4. The vertical axis in FIG. 4 represents amplitudes of the image spectrum. The two planar axes in FIG. 4 represent spatial frequencies in the axial space domain ($k_z$ domain) and the lateral space domain ($k_x$ domain).

Localized property: The spectrum of ultrasound image, in fact, is located and concentrated on some frequency area in both $k_x$ and $k_z$ domains. For example, the spectrum in FIG. 4 concentrates on two peak locations 401 and 402. The peak locations depend on: (i) sampling rate (or sample time duration) in time (i.e. axial (z) direction) and sampling rate in space (i.e. lateral (x) direction) and (ii) center frequency of the transducer 110. The bandwidth (BW) of the image spectrum depends on the above mentioned (i) sampling rate in time and space and (ii) fractional BW of the transducer 110. The higher sampling rate the ultrasound scanner provides, the narrower image BW we have.

Symmetric property: Due to the real-valued echo signal, the image spectrum is diagonally conjugated symmetric at the origin in axial (z) and lateral (x) directions. As shown in FIG. 4, the spectrum in quadrant 421 and the spectrum in quadrant 423 are symmetric. The spectrum in quadrant 422 and the spectrum in quadrant 424 are also symmetric.

Figure 5A:
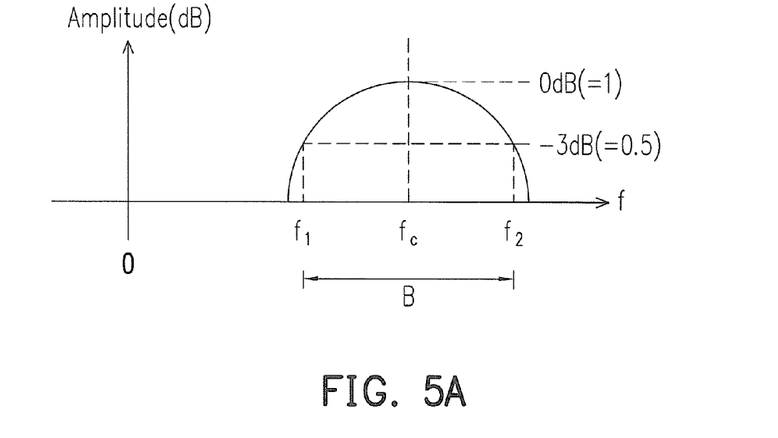
FIG. 5A is a schematic diagram showing the center frequency and the bandwidth of an ultrasound transducer according to an embodiment.
Figure 5B:
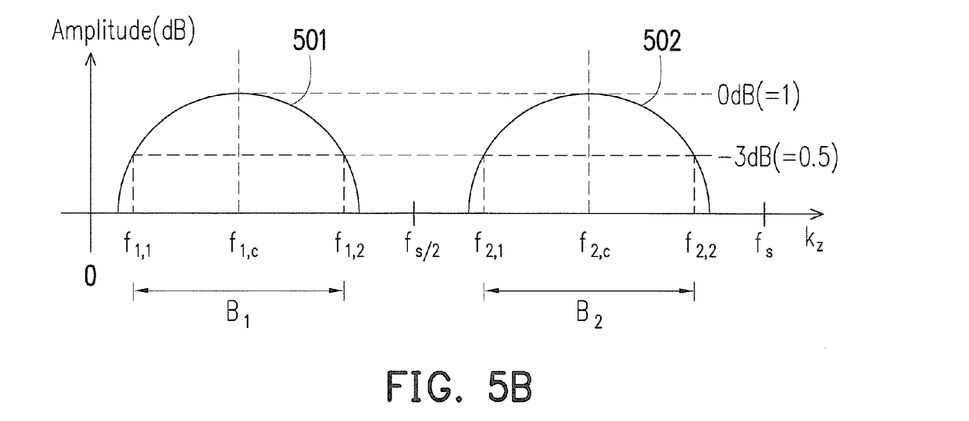
FIG. 5B is a schematic diagram showing an image spectrum in a space domain according to an embodiment.

FIG. 5A is a schematic diagram showing the center frequency $f_c$ and the bandwidth B of the transducer 110 according to an embodiment. FIG. 5B shows the resultant conjugated symmetric spectrum of an ultrasound image in $k_z$ domain according to this embodiment. Let $f_c$ be the center frequency of the transducer 110 and assume that $B=|f_2-f_1|$ is the BW of the transducer 110, where $f_2$ and $f_1$ are respectively the upper and lower 3-dB cutoff frequencies of the transducer 110. The spectrum in FIG. 5B includes two symmetric parts 501 and 502. $f_s$ is the sampling rate of the transducer 110. $f_{1,c}$ and $f_{2,c}$ are the center frequencies of the parts 501 and 502. $B_1=|f_{1,2}-f_{1,1}|$ and $B_2=|f_{2,2}-f_{2,1}|$ are the bandwidths of the two spectrum parts 501 and 502. $f_{1,2}$ and $f_{1,1}$ are respectively the upper and lower 3-dB cutoff frequencies of the spectrum part 501. $f_{2,2}$ and $f_{2,1}$ are respectively the upper and lower 3-dB cutoff frequencies of the spectrum part 502.

From above discussions, it can be shown that the image spectrum indeed is located within some frequency area in both the $k_x$ and $k_z$ domains. Based on the property, it is intuitive to perform a spectral analysis (via the Fourier transform) on a specific frequency band (band of interest, BOI) corresponding to one of the two symmetric parts 501 and 502, instead of performing the spectral analysis on the overall frequency range, for computational and performance consideration. It thus motivates the use of the spectrum zooming technique in the ZFFT in step 243.

Figure 6A:
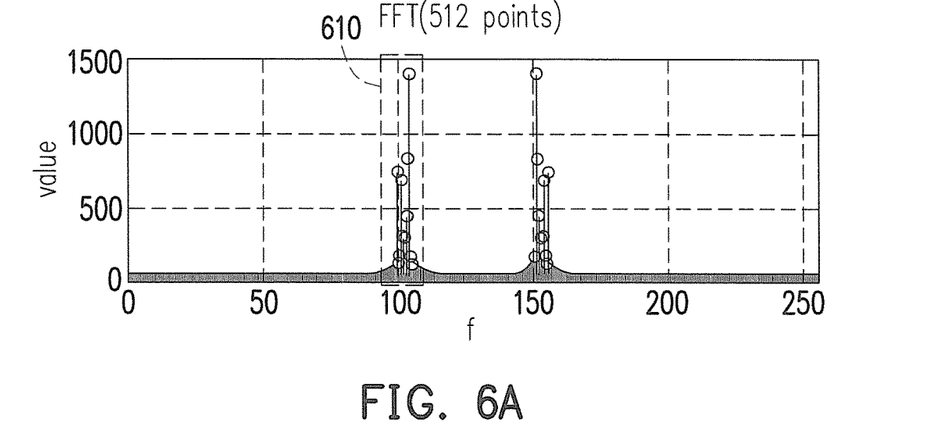
FIG. 6A, FIG. 6B and FIG. 6C are schematic diagrams showing spectrum zooming according to an embodiment.
Figure 6B:
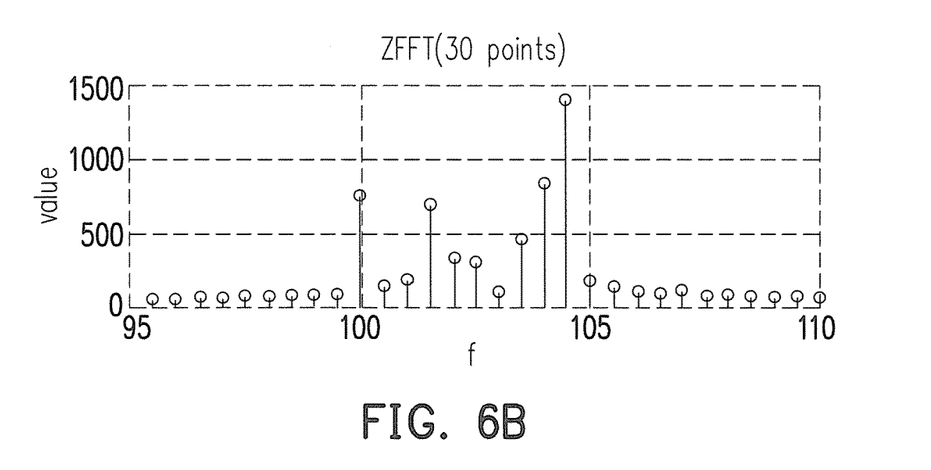
Figure 6C:
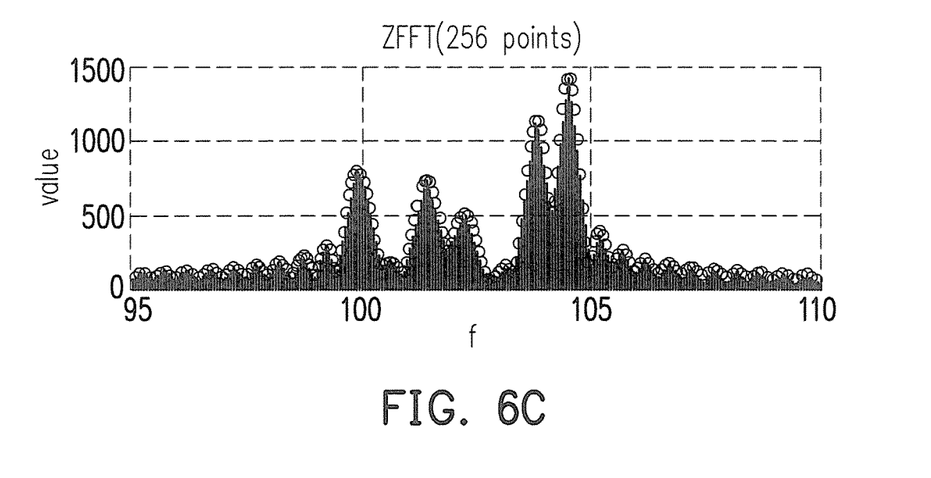

Spectrum refinement (i.e. better frequency resolution and better image performance) w.r.t. the BOI can be done by using a larger sample size of Fourier transform to create more useful information. This is shown in FIG. 6A, FIG. 6B and FIG. 6C. FIG. 6A depicts a spectrum (via 512-point FFT) of an exemplary time-domain signal with sample length of 512. It can be shown from FIG. 6A that the spectral signal of interest (SOI) between frequency indices 96-110 somehow is roughly located in part of the overall frequency range. But if the spectrum is zoomed-in (i.e. performed by ZFFT) into a BOI 610 (the 30 spectral lines between frequency indices 96-110), the profile of corresponding spectra (i.e. SOI) can be a little clearly defined as shown in FIG. 6B. However, no additional information is created so the capability of spectra identification (i.e. frequency resolution) cannot be improved. To enhance the frequency resolution, it needs to further refine the SOI by using a larger size of ZFFT over the BOI. Length-256 ZFFT in FIG. 6C illustrates that the SOI indeed has clearer and more detailed spectral profile. As a result, it provides a better capability of spectra identification.

Figure 7:
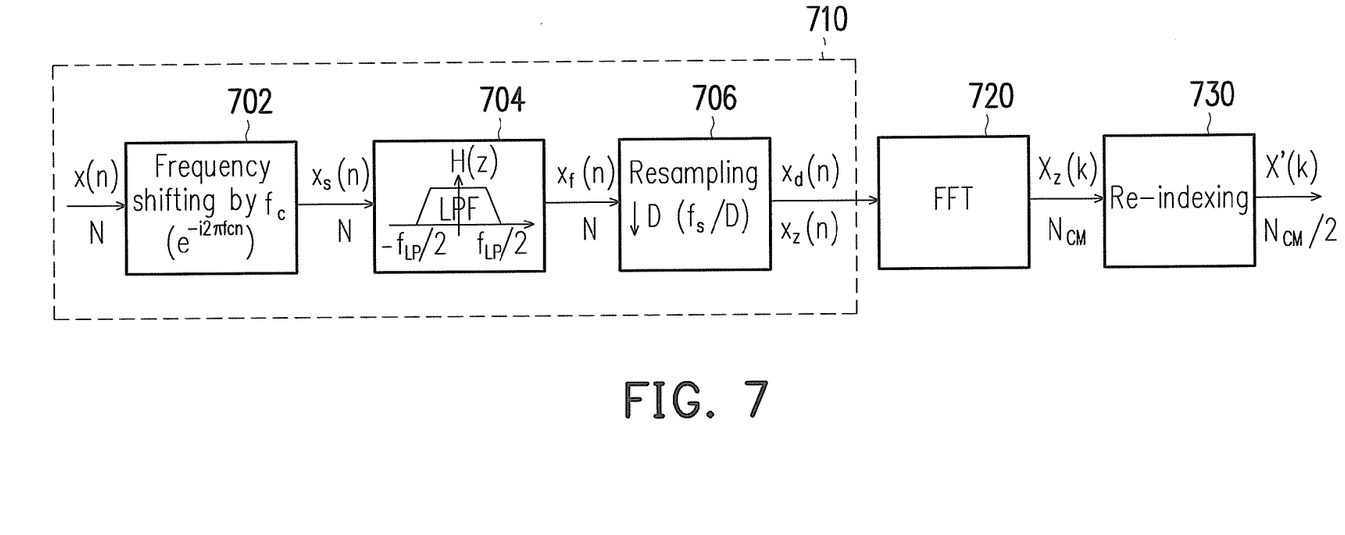
FIG. 7 is a flow chart showing spectrum zooming and Fourier transform according to an embodiment.

FIG. 7 is a flow chart showing details of the ZFFT in step 243 according to an embodiment. The ZFFT includes the spectrum zooming step 710 and the FFT step 720. The spectrum zooming step 710 includes steps 702, 704 and 706. In this embodiment, complex modulation (CM) is used for spectrum zooming. The overall procedures are described as follows. Assume that x(n), n=1, 1, . . . , N, is a discrete-time real-valued signal with a sample frequency $f_s$, and the SOI is located around $f_c$ with a bandwidth B, where N is the number of samples. In step 702, x(n) is first modulated into a complex-valued one $x_s(n)$ by a frequency shift of $f_c$, $e^{-i2\pi f_c n}$ to the base band. In other words, the SOI is shifted from the BOI to the base band. Then in step 704 $x_s(n)$ is filtered using an ideal low-pass filter (LPF) H(z) with length of Q and cut-off frequency $f_{LP}/2$ to obtain $x_f(n)$, where $f_{LP} \geq B$. In step 706, down-sampling $x_f(n)$ by a rate of D leads to a zoom-in signal $x_d(n)$ so that the sample frequency now becomes $f_s/D$ and the length of $x_d(n)$ becomes N/D. This shows that zooming in a signal results in a reduced-length output and thus lower computational time. However, D should be used with the condition $BD \leq f_s/2$ to avoid data miss. Then $x_d(n)$ is zero padded to form $x_z(n)$ with $N_{CM}=2^p$ ($\geq$N/D) samples if needed for the FFT process in step 720, where p is a positive integer. Next, performing FFT on $x_z(n)$ in step 720 gives the spectrum $X_z(k)$ and re-indexing $X_z(k)$ in step 730 obtains a half-length final output spectrum X'(k).

Figure 8:
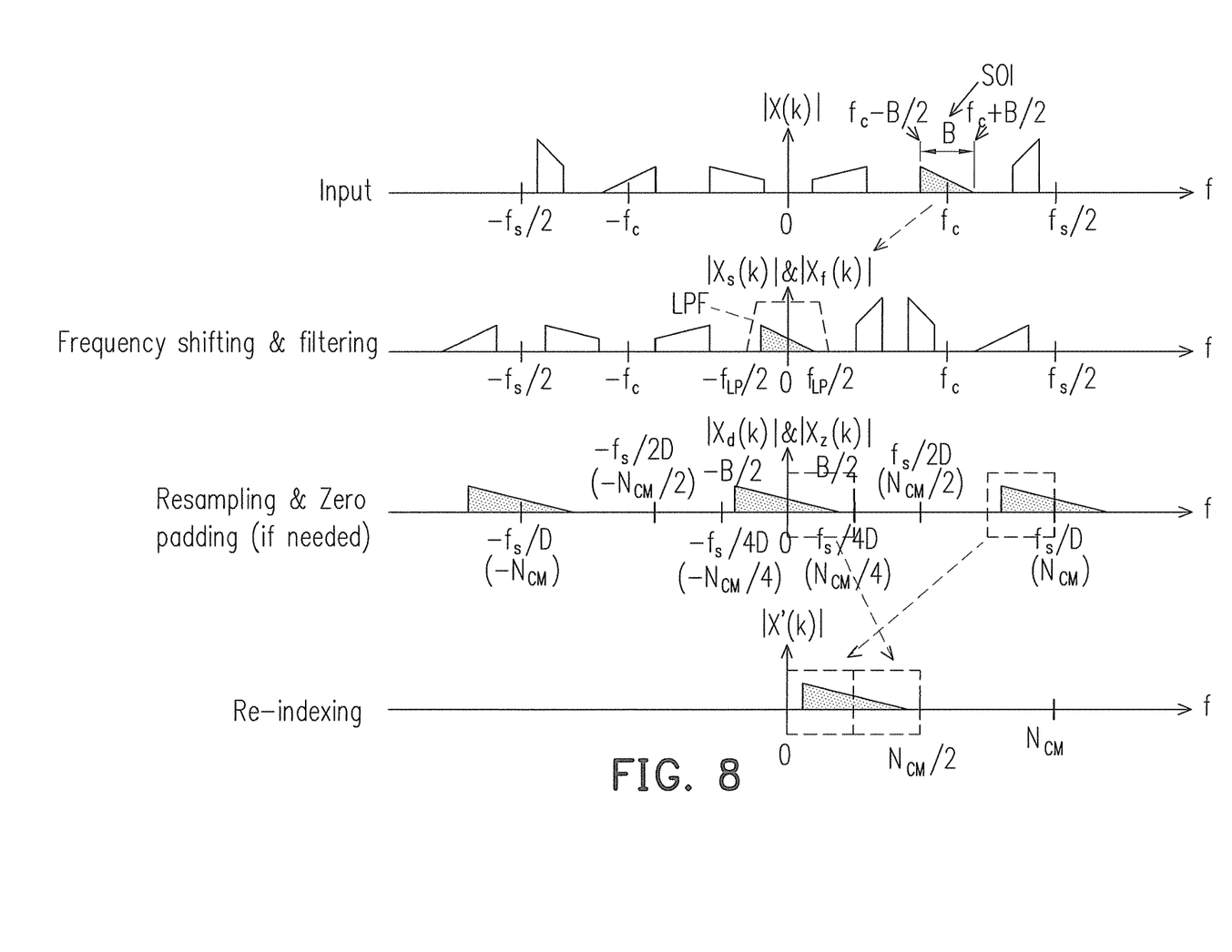
FIG. 8 is a schematic diagram showing spectrum zooming and Fourier transform according to an embodiment.

In ZFFT, the spectrum zooming process is completed in three steps: frequency shifting (step 702), low-pass filtering (step 704) and resampling (step 706), and the action of the zooming is done in step 706. To facilitate the understanding, the overall procedures of the CM for ZFFT in frequency domain are depicted in FIG. 8.

Figure 9:
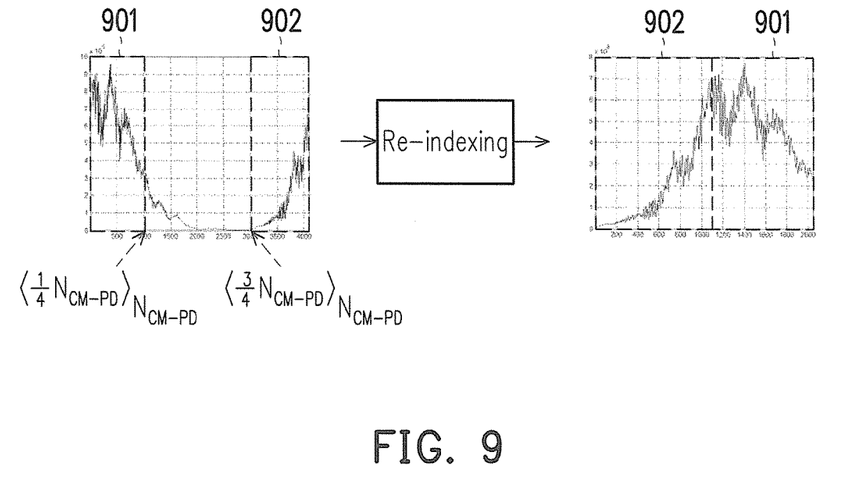
FIG. 9 is a schematic diagram showing re-indexing according to an embodiment.

It is known that the output sequence of $N_{CM}$-point FFT will be periodic with period $N_{CM}$ and circularly shifted by a number of units in frequency due to the frequency shift by $f_c$ and zero padding for accommodation of power-of-2 FFT size as mentioned above. To adequately obtain the half-length in-order final output spectrum data for further ultrasound imaging, the re-indexing in step 730 is thus needed. FIG. 9 is a schematic diagram showing the re-indexing in step 730 according to an embodiment. This re-indexing can be done by partially selecting the last $$\left\langle \frac{3}{4} N_{CM} \right\rangle_{N_{CM}}$$

samples 902 (i.e. the ending part) and then the first $$\left\langle \frac{1}{4} N_{CM} \right\rangle_{N_{CM}}$$

samples 901 (i.e. the beginning part) of the output sequence of the FFT in step 720, respectively, and combining them as illustrated in the right part of FIG. 9, where $\langle \bullet \rangle_N$ is mod N operation.

It is well known that in CM based ZFFT the LPF step 704 and the down-sampling step 706 can be realized by polyphase decomposition (PD) for computational efficiency. Without loss of generality, assume that PD of LPF H(z) with length of Q can be expressed as the following equation (2).

$$H(z) = \sum_{n=0}^{Q-1} h(n) z^{-n} = \sum_{d=0}^{D-1} z^{-d} E_d(z^D) \qquad (2)$$

In equation (2), $E_d(z^D)$ is the dth polyphase component of H(z) with length of L=Q/D. The dth polyphase component $E_d(z^D)$ can be expressed as the following equation (3), and then equation (4) can be obtained.

$$E_d(z^D) = \sum_{l=0}^{L-1} h(lD+d)(z^D)^{-l} \qquad (3)$$

$$H(z) = \sum_{d=0}^{D-1} z^{-d} \sum_{l=0}^{L-1} h(lD+d)(z^D)^{-l} \qquad (4)$$

Figure 10:
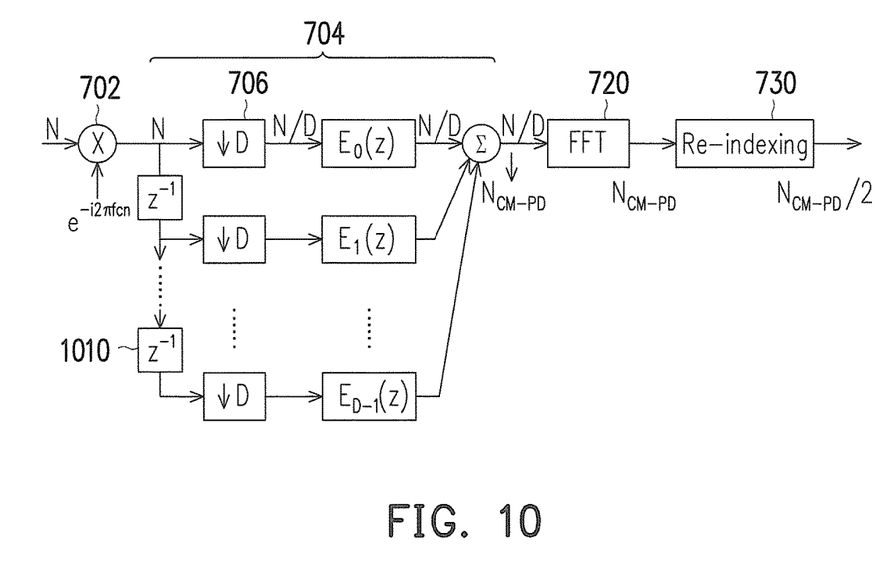
FIG. 10 is a schematic diagrams showing spectrum zooming and Fourier transform according to another embodiment.

From equations (2) and (3) and using the input-output equivalence of the LPF step 704 and the down-sampling step 706, where performing down-sampling after LPF equals to performing LPF after down-sampling, LPF with down-sampling, can then be implemented by a structure of a set of filter banks as depicted in FIG. 10. In particular, the computational complexity of performing LPF after down-sampling is lower than that of performing down-sampling after LPF due to the less input samples (N/D instead of N) to the polyphase component $E_d(z^D)$ of LPF H(z). This leads to a computationally efficient structure on the PD shown in FIG. 10 for CM based ZFFT.

Each $z^{-1}$ block in FIG. 10, such as the block 1010, represents a one-sample delay. The filter banks in FIG. 10 include D branches and each branch corresponds to a branch signal. The first branch signal is the SOI through the frequency shift 702. Each of the other branch signals is the previous branch signal through a one-sample delay. The down-sampling 706 is performed on each branch signal. A polyphase component of the LPF H(z) is applying on each branch signal. After the down-sampling and the polyphase components, the branch signals of the branches are added together to form the result of the spectrum zooming. The sample size before the zero padding for FFT is N/D, while the sample size after the zero padding is $N_{CM-PD}$. $N_{CM-PD}$ is a power of two.

Due to the filter banks structure, the CM method realized by PD solution (called the CM-PD method) provides (i) computational efficiency and (ii) parallel computing compared to the original CM one.

Figure 11:
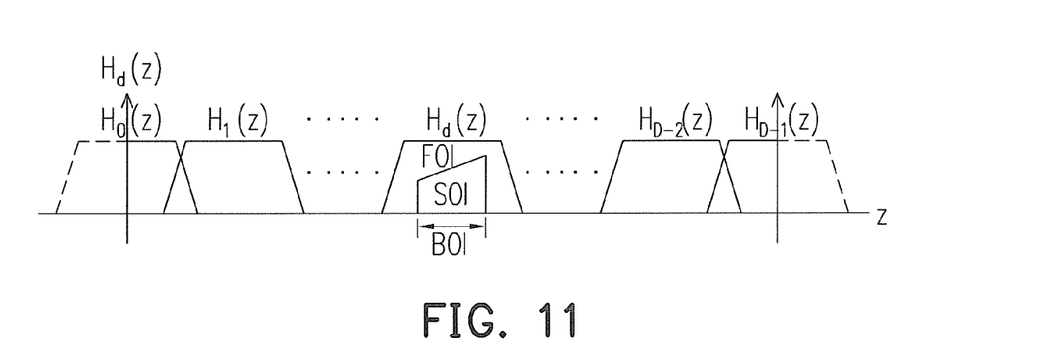
FIG. 11 and FIG. 12 are schematic diagrams showing spectrum zooming and Fourier transform according to another embodiment.

Recall that in CM method, the discrete-time signal x(n) is first modulated by a frequency shift $e^{-i2\pi f_c n}$ to the complex base band and then passed into the LPF. This somehow induces a computational burden due to a complex-valued data input to the LPF. A method called discrete Fourier transform (DFT) filter banks (DFBs), however, does not need the complex modulation operation in the spectrum zooming. The basic idea of this method is to use the DFBs to separate the overall bandwidth into D sub-bands and then select the BOI for further spectral analysis, so additional DFT operation compared to CM method is thus be needed. The operation of separating the overall bandwidth into D sub-bands can be done by using a set of parallel uniform filters (PUFs) $H_0(z)$, $H_1(z)$ . . . $H_{D-1}(z)$ shown in FIG. 11. Assume that, for simplicity, the SOI is located in a specific sub-band (i.e. BOI), and let the BOI be, for example, the dth sub-band. Then the SOI can be picked up by the dth filter $H_d(z)$ (i.e. band-pass filter (BPF)) (called the filter of interest (FOI)), which can be generated by a rotation (phase shift) version $e^{-i2\pi d/D}$ of the $0^{th}$ filter $H_0(z)$ (i.e. LPF) with length of Q according to the following equation (5).

$$H_d(z) = H_0(z \cdot e^{-i2\pi d/D}) = H_0(z \cdot W_D^d), d = 0, 1, \ldots, D-1 \quad (5)$$

Similarly, as mentioned above, the LPF $H_0(z)$ can be realized by the PD solution for computational efficiency, that is, $$H_0(z) = \sum_{n=0}^{Q-1} h(n)z^{-n} = \sum_{j=0}^{D-1} z^{-j} E_j(z^D) \quad (6)$$

where $E_j(z^D)$ is the jth polyphase component of $H_0(z)$ with length of L=Q/D. Substituting equation (6) into equation (5), we have the following equation (7).

$$H_d(z) = \sum_{j=0}^{D-1} (zW_D^d)^{-j} E_j(z^D) = \sum_{j=0}^{D-1} z^{-j} E_j(z^D) \cdot (W_D^{-jd}), \quad (7)$$
$$d = 0, 1, \ldots, D-1$$

Figure 12:
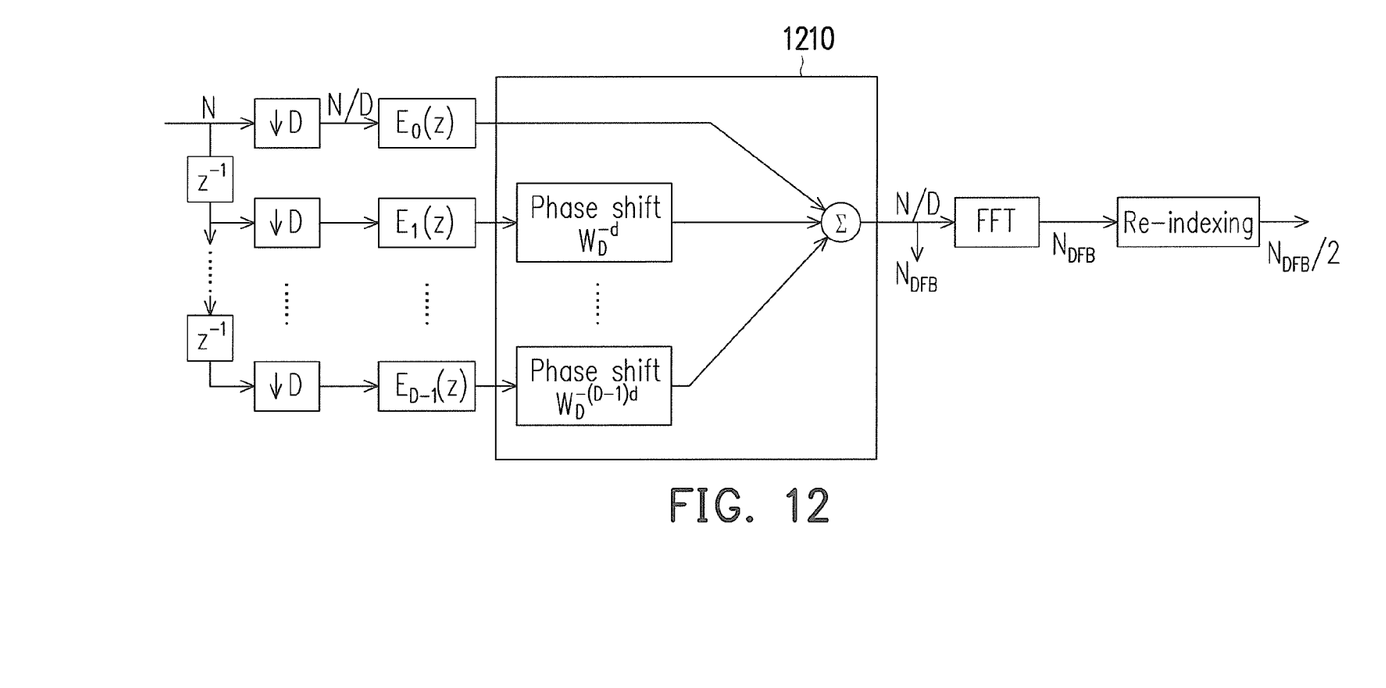

From equation (7), it can be seen that the SOI (i.e. in the dth sub-band) can be picked up by (i) polyphase component of LPF, $E_j(z^D)$, and (ii) DFT operation based on rotation factor $W_D^{-jd}$, j=1, 2, . . . , D−1. From equation (7) and referring to the CM method, the overall ZFFT schematic diagram based on the DFBs is shown in FIG. 12. In particular, it also shows that the spectrum zooming eventually is completed by D-branch PD and D-point DFT.

FIG. 12 is a schematic diagram showing the ZFFT in step 243 based on the aforementioned DFB method. According to FIG. 12, a plurality of branch signals is generated. The first branch signal is the SOI and each of the other branch signals is the previous branch signal through a one-sample delay. The down-sampling is performed on each branch signal. A polyphase component of the BPF is applied on each branch signal. After the down-sampling and the polyphase components, a DFT 1210 is performed on the branch signals to form the result of the spectrum zooming. The sample size before the zero padding for FFT is N/D, while the sample size after the zero padding is $N_{DFB}$. $N_{DFB}$ is a power of two.

Figure 13:
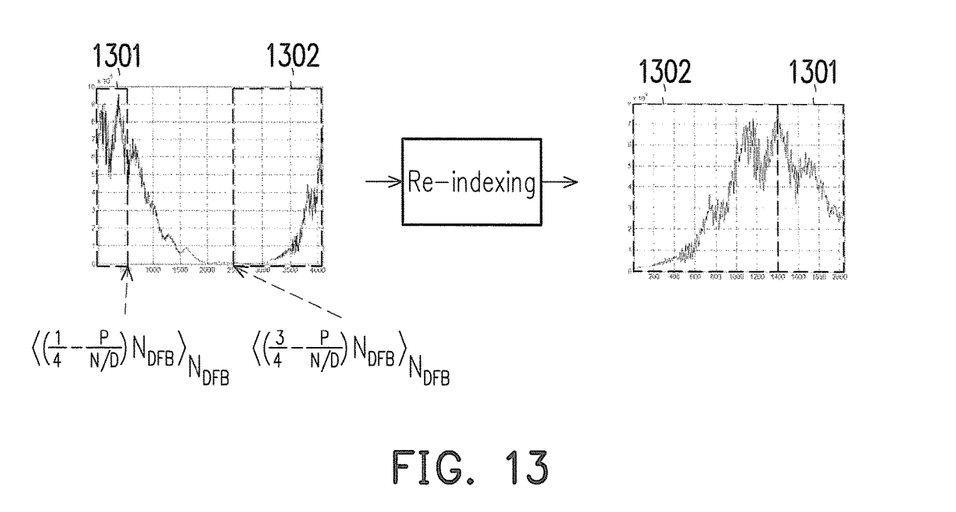
FIG. 13 is a schematic diagram showing re-indexing according to an embodiment.

Similar to the CM method, the result of the spectrum zooming may be zero-padded for accommodation of a power-of-2 FFT size $N_{DFB}$. Due to the zero padding, re-indexing is needed to adequately get the half-length in-order final output spectrum data for further ultrasound imaging. FIG. 13 is a schematic diagram showing the re-indexing according to an embodiment. The re-indexing is done by partially selecting the last $$\left\lfloor \left(\frac{3}{4} - \frac{P}{N/D}\right) N_{DFB} \right\rfloor_{N_{DFB}}$$

samples 1302 (i.e. the ending part) and then the first $$\left\lfloor \left(\frac{1}{4} - \frac{P}{N/D}\right) N_{DFB} \right\rfloor_{N_{DFB}}$$

samples 1301 (i.e. the beginning part) of the FFT output sequences, respectively, and combining them as illustrated in the right part of FIG. 13, where $$P = \frac{f_c}{f_s} N.$$

Similar to the CM-PD method, due to the filter banks structure, the DFB method also provides (i) computational efficiency and (ii) parallel computing compared to the original CM method.

Figure 14A:
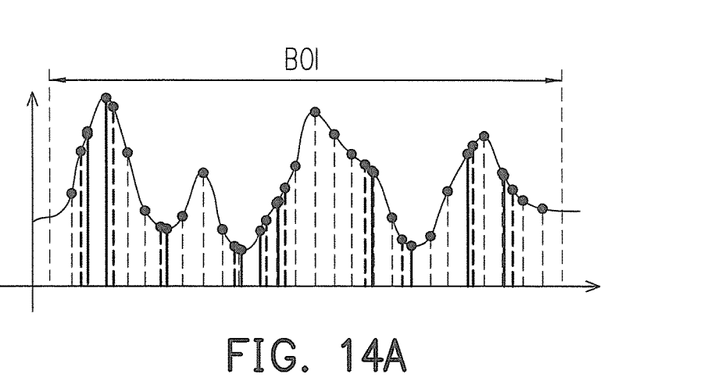
FIG. 14A is a schematic diagram showing spectra identification according to an embodiment.

FIG. 14A is a schematic diagram showing the spectra identification in step 246 according to an embodiment. The result of the FFT after the re-indexing includes a plurality of source spectral lines. In FIG. 14A, the thin dotted spectral lines and the thick solid spectral lines are the source spectral lines. The source spectral lines are uniformly distributed in the axial space domain ($k_z$ domain). The purpose of the spectra identification in step 246 is estimating a plurality of target spectral lines required by the IFFT in step 250 according to the source spectral lines. In FIG. 14A, the target spectral lines are the thick dotted spectral lines.

The target spectral lines are non-uniformly distributed in the axial space domain ($k_z$ domain). Positions of the target spectral lines along the $k_z$ axis can be determined by the equation (1). Since the target spectral lines are non-uniformly distributed, the target spectral lines cannot be obtained directly from the source spectral lines. In this embodiment, the target spectral lines are estimated by nearest neighbor search (direct search) based on the source spectral lines. As shown in FIG. 14A, for each target spectral line, there is a corresponding source spectral line nearby. The corresponding source spectral lines are shown as thick solid lines in FIG. 14A. For each target spectral line, its corresponding source spectral line is the source spectral line nearest to that target spectral line. In this embodiment, the corresponding source spectral lines are input to the following step 250 (in FIG. 2A) or step 230 (in FIG. 2B) to serve as the target spectral lines.

Figure 14B:
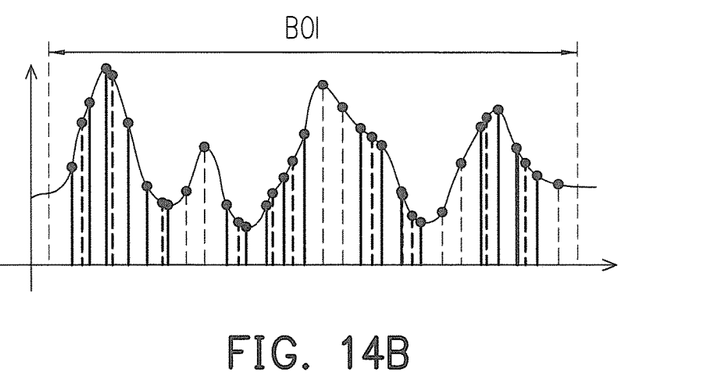
FIG. 14B is a schematic diagram showing spectra identification according to another embodiment.

FIG. 14B is a schematic diagram showing the spectra identification in step 246 according to another embodiment. In this embodiment, the target spectral lines are estimated by interpolation based on the source spectral lines. As shown in FIG. 14B, for each target spectral line, there are two corresponding source spectral line nearby. The corresponding source spectral lines are shown as thick solid lines in FIG. 14B. For each target spectral line, its corresponding source spectral lines are the two source spectral lines nearest to that target spectral line. In this embodiment, each target spectral line is calculated by interpolation based on the two corresponding source spectral lines. The target spectral lines are input to the following step 250 (in FIG. 2A) or step 230 (in FIG. 2B).

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A method of ultrasound imaging, including:
   receiving an echo signal induced by an ultrasonic plane wave transmission from a transducer of an ultrasound scanner;
   resampling the echo signal in time domain and/or space domain;
   performing a spectrum zooming on a band of interest (BOI) of an input signal, wherein the input signal is generated based on the resampling of the echo signal wherein the spectrum zooming includes performing a frequency shift to shift a signal of interest (SOI) of the input signal from the BOI to a base band; generating a plurality of branch signals based on the shifted SOI, wherein a first branch signal of the branch signals is the shifted SOI and each branch signal of the branch signals other than the first branch signal is a previous branch signal being generated by a one-sample delay; applying a low-pass filter (LPF) on each of the branch signals; and performing a down-sampling on each of the branch signals;
   performing a first Fourier transform on a result of the spectrum zooming;
   estimating a plurality of target spectral lines according to a plurality of source spectral lines included in the result of the first Fourier transform;
   performing an inverse Fourier transform based on the target spectral lines; and
   generating an ultrasound image by converting signal amplitudes of a result of the inverse Fourier transform into gray level values of pixels of the ultrasound image.

2. The method of claim 1, wherein the BOI includes one of two symmetric parts of a spectrum of the input signal in an axial space domain.

3. The method of claim 1 further includes:
   applying a polyphase component of the LPF on each of the branch signals; and
   after the down-sampling and the polyphase components of each of the branch signals, adding each of the branch signals to form the result of the spectrum zooming.

4. The method of claim 1, wherein the spectrum zooming includes:
   applying a band-pass filter (BPF) on an SOI of the input signal in the BOI; and
   performing a down-sampling on the SOI.

5. The method of claim1, wherein the spectrum zooming includes:
   applying a polyphase component of an LPF on each of the branch signals; and
   after the down-sampling and the polyphase components, performing a discrete Fourier transform (DFT) on the plurality of branch signals to form the result of the spectrum zooming.

6. The method of claim 1, further including:
   re-indexing an output sequence of the first Fourier transform by putting a beginning part of the output sequence after an ending part of the output sequence to form the result of the first Fourier transform.

7. The method of claim 1, further including:
   performing a second Fourier transform based on the resampling of the echo signal, wherein the first Fourier transform is corresponding to an axial direction with respect to the transducer and the second Fourier transform is corresponding to a lateral direction with respect to the transducer, the axial direction and the lateral direction are orthogonal, and the input signal is generated by the second Fourier transform.

8. The method of claim 1, further including:
   performing a second Fourier transform based on the result of the first Fourier transform, wherein the first Fourier transform is corresponding to an axial direction with respect to the transducer and the second Fourier transform is corresponding to a lateral direction with respect to the transducer, the axial direction and the lateral direction are orthogonal, and the ultrasound image is generated based on the result of the first Fourier transform and the second Fourier transform.

9. The method of claim 1, wherein the target spectral lines are non-uniformly distributed in an axial space domain, the source spectral lines are uniformly distributed in the axial space domain, and the ultrasound image is generated based on the target spectral lines.

10. The method of claim 1, further including:
    estimating the target spectral lines by nearest neighbor search based on the source spectral lines.

11. The method of claim 1, further including:
    estimating the target spectral lines by interpolation based on the source spectral lines.

12. An ultrasound scanner, including:
    a transducer; and
    a processor, coupled to the transducer, configured to receive an echo signal induced by an ultrasonic plane wave transmission from the transducer, resample the echo signal in time domain and/or space domain, perform a spectrum zooming on a band of interest (BOI) of an input signal, wherein the spectrum zooming includes performing a frequency shift to shift a signal of interest (SOI) of the input signal from the BOI to a base band; generating a plurality of branch signals based on the shifted SOI, wherein a first branch signal is the shifted SOI and wherein each branch signal of the branch signals other than the first branch signal is a previous branch signal being generated by a one-sample delay; applying a low-pass filter (LPF) on each of the branch signals; and
    performing a down-sampling on each of the branch signals, wherein the processor performs a first Fourier transform on a result of the spectrum zooming, wherein the input signal is generated based on the resampling of the echo signal, wherein the processor is configured to estimate a plurality of target spectral lines according to a plurality of source spectral lines included in the result of the first Fourier transform, wherein the processor is configured to perform an inverse Fourier transform based on the target spectral lines, and the processor is configured to generate an ultrasound image by converting signal amplitudes of a result of the inverse Fourier transform into gray level values of pixels of the ultrasound image.

13. The ultrasound scanner of claim 12, wherein the BOI includes one of two symmetric parts of a spectrum of the input signal in an axial space domain.

14. The ultrasound scanner of claim 12, wherein the processor is further configured to apply a polyphase component of the LPF on each of the branch signals, and after the down-sampling and the polyphase components of each of the branch signals, the processor is configured to add each of the branch signals to form the result of the spectrum zooming.

15. The ultrasound scanner of claim 12, wherein for performing the spectrum zooming, the processor is configured to apply a band-pass filter (BPF) on an SOI of the input signal in the BOI, and perform a down-sampling on the SOI.

16. The ultrasound scanner of claim 12, wherein the processor is configured to apply a polyphase component of an LPF on each of the branch signals, and after the downsampling and the polyphase components, the processor is configured to perform a discrete Fourier transform (DFT) on the plurality of branch signals to form the result of the spectrum zooming.

17. The ultrasound scanner of claim 12, wherein the processor s configured to re-index an output sequence of the first Fourier transform by putting a beginning part of the output sequence after an ending part of the output sequence to form the result of the first Fourier transform.

18. The ultrasound scanner of claim 12, wherein the processor is configured to perform a second Fourier transform based on the resampling of the echo signal, the first Fourier transform is corresponding to an axial direction with respect to the transducer and the second Fourier transform is corresponding to a lateral direction with respect to the transducer, the axial direction and the lateral direction are orthogonal, and the input signal is generated by the second Fourier transform.

19. The ultrasound scanner of claim 12, wherein the processor is configured to perform a second Fourier transform based on the result of the first Fourier transform, the first Fourier transform is corresponding to an axial direction with respect to the transducer and the second Fourier transform is corresponding to a lateral direction with respect to the transducer, the axial direction and the lateral direction are orthogonal, and the processor is configured to generate the ultrasound image based on the result of the first Fourier transform and the second Fourier transform.

20. The ultrasound scanner of claim 12, wherein the target spectral lines are non-uniformly distributed in an axial space domain, the source spectral lines are uniformly distributed in the axial space domain, and the processor generates the ultrasound image based on the target spectral lines.

21. The ultrasound scanner of claim 12, wherein the processor is configured to estimate the target spectral lines by nearest neighbor search based on the source spectral lines.

22. The ultrasound scanner of claim 12, wherein the processor is configured to estimate the target spectral lines by interpolation based on the source spectral lines.

* * * * *